United States Patent
Joshi et al.

(10) Patent No.: US 6,846,932 B1
(45) Date of Patent: Jan. 25, 2005

(54) PROCESS FOR PREPARATION OF CHIRAL AMLODIPINE SALTS

(75) Inventors: Rohini R. Joshi, Maharashtra (IN); Ramesh A. Joshi, Maharashtra (IN); Nilesh B. Karade, Maharashtra (IN); Mukund K. Gurjar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/718,267

(22) Filed: Nov. 20, 2003

(51) Int. Cl.⁷ .............................................. C07D 211/86
(52) U.S. Cl. ...................................................... 546/321
(58) Field of Search ........................................ 546/321

(56) References Cited

U.S. PATENT DOCUMENTS 6,046,338 A * 4/2000 Spargo ........................ 546/322
6,608,206 B1 * 8/2003 Joshi et al. .................. 546/321

* cited by examiner

*Primary Examiner*—Patricia L. Morris
(74) *Attorney, Agent, or Firm*—Darby & Darby

(57) ABSTRACT

A process for the preparation of pharmaceutically acceptable salts of chiral Amlodipine namely S(−) Amlodipine and R(+) Amlodipine from without isolation of a free base from with optical purity rank between 96–99% is described in the present invention. The process comprises resolving RS amlodipine base using of L(+) or D(−) tartaric acid to obtain salt of corresponding to the acid used in ee rang from 96–99%.

11 Claims, No Drawings

PROCESS FOR PREPARATION OF CHIRAL AMLODIPINE SALTS

FIELD OF THE INVENTION

The present invention relates to an improved process for the preparation of chiral amlodipine salts. More particularly, the present invention relates to the a process for the preparation of pharmaceutically acceptable salts of S (−) Amlodipine having formula (1) and R(+) Amlodipine having formula (2) wherein R=benzenesulphoinic acid, succinic acid, maleic acid, oxalic acid, p-toluene sulphonic, acid as given hereinbelow in the presence of dimethylsulfoxide and their direct conversion to besylate without isolating free base.

FORMULA-1

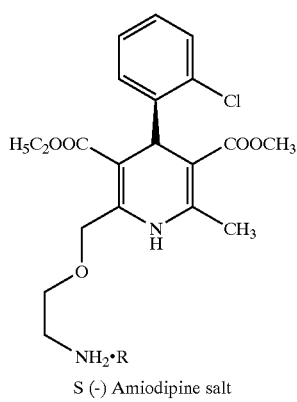

S (−) Amiodipine salt

FORMULA-2

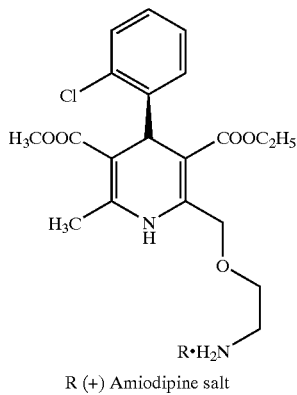

R (+) Amiodipine salt

BACKGROUND OF THE INVENTION

Of all the salts of S (−) Amlodipine mentioned above, S (−) Amlodipine besylate (4-S)-2-{[(2-aminoethyl)oxy]methyl}-4-(2-chlorophenyl)-6-methyl-1,4-dihydropyridine-3,5-dicarboxylate benzene sulfonate has commercial importance as a potent long acting calcium channel blocker.

R(+) Amlodipine has been reported as a potent inhibitor of smooth muscle cell migration (PCT/EP-94/02697). (R, S) amlodipine and its salts are long acting calcium channel blockers and are useful for the treatment of cardiovascular disorders. Racemic amlodipine is currently being used for the treatment of hypertension and angina as a besylate salt. The preparation of racemic compound is described in EP 0089167. Amlodipine is racemic compound and has chiral center at 4 position of dihydropyridine ring. The S(−) isomer is having calcium channel blocker activity while R(+) isomer is a potent inhibitor of smooth muscle cell migration.

Prior arts herein for the preparation of R and S enantiomers are a) resolution of amlodipine azide ester with optically active 2-methoxy-2-phenylethanol (J. Med. Chem. 29, 1696, 1986, EP appl. 0331315 A) or b) resolution of amlodipine base with optically active camphanic acid (J. Med. Chem. 35, 3341, 1992) c) resolution of R S amlodipine base with L (+) or D(−) tartaric acid respectively in organic solvent DMSO (USP 6,046,338 (2000) PCT95/25722 1995) d) resolution of penultimate azidoester precursor of amlodipine using cinchonidine. (USP 6,291, 490(2001), Chem. Pharm. Bull. 28 (9), 2809–2812, 1980).

Preparation of S(−) amlodipine besylate has been disclosed in the publication (J. Chem. B., 693, 1997, 367–375, followed by fully described and claimed in out co-pending patent application no. NF347/02 which relates to the process for the preparation of pharmaceutically acceptable salts of S(−) Amlodipine such as besylate, succinate, maleate, oxalate and tosylate from S(−) Amlodipine.

The main disadvantages of the prior art are:

1. The use of costly resolving agents like camphanic acid, 2-methoxy-2-phenylethanol, cinchonidine.
2. The use of 0.5 mole of L (+) or D(−) tartaric acid increasing the load of recovery of tartaric acid.
3. Low yield of isolated resolved salt using less quantities of resolving agent.
4. Use of large volumes of solvent (1:10)
5. Isolation of free chiral base from the salt and treatment with benzene sulfonic acid to get besylate salt.

OBJECTS OF THE INVENTION

The object of present invention is to provide a process for the preparation of S(−) and R(+) Amlodipine besylate frpom racemic amlodipine using D or L tartaric acid without isolating free amlodipine base

SUMMARY OF THE INVENTION

Accordingly, the present invention provides an improved process for the preparation of pharmaceutically acceptable chiral salts of Amlodipine namely S(−) Amlodipine salts having formula (1) and R(+) Amlodipine salts having formula (2)

FORMULA-1

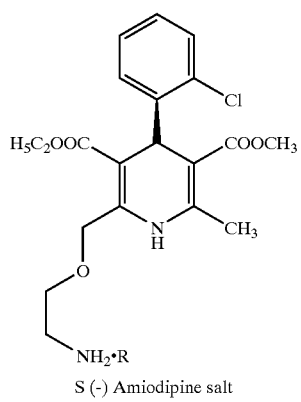

S (−) Amiodipine salt

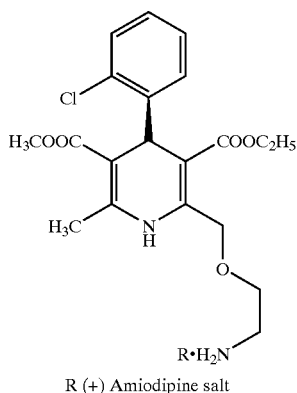

R (+) Amlodipine salt

FORMULA-2 wherein R is selected from the group consisting of benzenesulphoinic acid, succinic acid, maleic acid, oxalic acid and p-toluenesulphonicacid, wherein the salts of formula 1 and 2 are prepared without isolation of a free base with optical purity ranging between 96–99% the process comprising
(a) reacting a solution of RS amlodipine base in an: organic solvent with a solution of L(+) or D(−) tartaric acid in an organic solvent at temperature ranging from 20–35° C. for a period ranging between 16–24 hrs., to obtain a solvate comprising an amlodipine tartarate salt;
(b) separating and reacting the amlodipine tartarate salt obtained in step (a) with an aqueous solution of an acid optionally in presence of an organic solvent, and at a temperature ranging between 2040° C.;
(c) adding water to the reaction mixture of step (b) to obtain the salt of formula 1 or 2, separating the salt of formula 1 or 2 and drying to obtain salt corresponding to the acid used in step (2) with ee ranging from 96–99%.

In one embodiment of the invention, the solvent used in step (a) is DMSO.

In another embodiment of the invention, the concentration of RS amlodipine base to solvent (DMSO) ranges between 0.16 to 0.40 gm/ml.

In yet another embodiment of the invention, L(+)-tartaric acid or D(−) tartaric acid employed is 0.25 mole equivalent of the amlodipine base.

In a further embodiment of the invention, the solvate obtained in step (a) is a precipitate comprising S(−) Amlodipine hemi D(−) tartarate mono DMSO solvate or R(+) amlodipine hemi L(+) tartarate mono DMSO solvate.

In another embodiment of the invention, the solvent used for salt formation in step (b) is selected from dimethylsulfoxide, isopropylacohol and ethanol.

In another embodiment of the invention, the ratio of water to solvent cumulatively taken in steps (b) and (c) ranges between 5;1 to 8:1.

In yet another embodiment of the invention, the acid used in step (b) is selected from the group consisting of benzenesulfonic, maleic, oxalic acid and p-toluene sulfonic acid.

In another embodiment of the invention, the ratio of amlodipine tartarate salt to organic solvent in step (b) is in the range 1:1 to 1:5.

In another embodiment of the invention, the mole equivalent of benzene sulfonic acid used ranges between 0.9 to 1.

In another embodiment of the invention, the optical purity of R(+) amlodipine besylate or S(−) amlodipine besylate is improved from 95% to 99%.

DETAILED DESCRIPTION OF THE INVENTION

The present invention provides a process for the preparation of pharmaceutically acceptable chiral Amlodipine salts comprising S(−) Amlodipine salts having formula (1) and R(+) Amlodipine salts having formula (2)

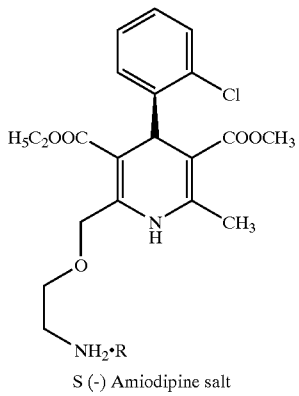

S (−) Amlodipine salt

FORMULA-1

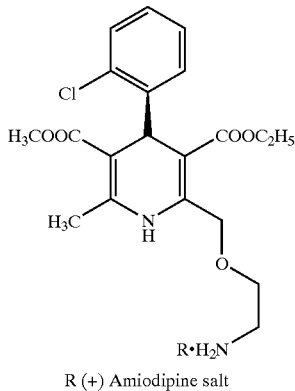

R (+) Amlodipine salt

FORMULA-2

In the above formulae 1 and 2, R is selected from the group costing of benzenesulphoinic acid, succinic acid, maleic acid, oxalic acid and p-toluene sulphonic acid. The salts of formula 1 and 2 are prepared without isolation of a free base with optical purity ranging between 96–99%.

The process of the invention comprises of
(a) reacting the solution of RS amlodipine base in an organic solvent with a solution of L(+) or D(−) tartaric acid in an organic solvent at temperature ranging from 20–35° C. for a period ranging between 16–24 hrs.
(b) separating the tartarate salt as obtain in step (a) and reacting the said salt with an aqueous solution of an acid optionally in presence of an organic solvent at a temperature ring between 2040° C.
(c) adding water to the reaction mixture as obtained in step (b) to obtain the salt, separating the salt and drying to obtain salt corresponding to the acid used in step (b) with ee ranging from 96–99%.

The solvent used in step (a) above is preferably dimethyl sulfoxide (DMSO) and the concentration of the RS amlodipine base to solvent (DMSO) ranges between 0.16 to 0.40 gm/ml. The L(+)-tartaric acid or D(−) tartaric acid employed in step (a) is 0.25 mole equivalent of the base. The tartars alt is obtained preferably by precipitation and the solvate precipitated is S(−) Amlodipine hemi D(−) tartarate mono DMSO solvate or R(+) amlodipine hi L(+) tartarate mono DMSO solvate. The solvent used for salt formation in step (b) is selected from dimethylsulfoxide, isopropylacohol or ethanol. The ratio of amlodipine salt to organic solvent in step (b) is in the range 1:1 to 1:5 for salt formation. The ratio of water to solvent cumulatively taken in steps (b) and (c) ranges between 5:1 to 8:1. The acid used in step (b) is selected from benzenesulfonic acid, maleic acid, oxalic acid, and p-toluene sulfonic acid. The mole equivalent of benzene sulfonic acid used ranges between 0.9 to 1.

The optical purity of R(+) amlodipine besylate or S(−) amlodipine besylate is improved from 95% to 99%

The unique feature of the invention is production of S(−) Amlodipine or R(+) amlodipine salts with high enantiomeric purity, in good yields (87–92%) with the quality required for preparation of pharmaceutically composition i.e. tablet formulation. The process of resolution of R,S amlodipine and besylate formation is shown in the scheme below:

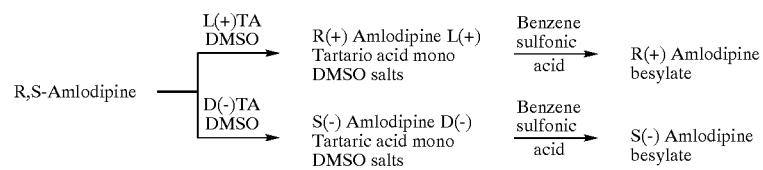

The process of the present invention is described herein below with reference to examples, which are illustrative and should not be construed to limit the scope of the present invention in any manner.

Optical purity (enantiomeric excess e.e.) was determined using chiral HPLC column: Chiral Chrompak 15 cm, ultron, The mobile phase used disodiumhydrogen phosphate buffer pH 6.9: acetonitile (80:20) with flow rate 1 ml/min at 360 nm Rt-R=6.1 min, S=7.3 min

EXAMPLE 1

R (+) Amlodipine Hemi L(+)Tartarate Mono DMSO Solvate from RS Amlodipine

To stirred solution of 10.50 gm (0.0256 mole) of RS amlodipine in 30 ml DMSO was added a solution of 1.93 gm (0.128 moles, 0.5 eq.) of L(+) tartaric acid in 30 ml DMSO. The solid starts separating from clear solution within 5–10 mins. This was stirred for 3 hrs and solid was filtered off, washed with acetone and dried to give 6.66 gm (46.2%) R(+) amlodipine hemi L(+) tartarate mono DMSO solvate. mp. 160162° C., 95.2% d.e. by chiral HPLC [J. Chrom. B. 693,367, (1997), J. Luksa, Dj. Josic, B. Podobric, B. Furlan, M. Kremser.]

EXAMPLE 2

R(+)Amlodipine HemiL(+) Tartarate Mono DMSO Solvate from RS Amlodipine

To a stirred solution of 100 gm (0.245 moles) of RS amlodipine in 300 ml DMSO was added a solution of 9.2 gm (0.06 moles, 0.25 eq) of L(+) tartaric acid in 300 ml DMSO. The solid starts separating from clear solution within 5–10 mins. This was stirred for 3 hrs and solid was filtered off, washed with acetone and dried to give 52.3 gm (36.2%) R(+) amlodipine hemi L(+) tartarate mono DMSO solvate. mp. 160.162° C., 98.2% d.e. by chiral HPLC.

EXAMPLE 3

R(+)Amlodipine HemiL(+)Tartarate Mono DMSO Solvate from RS Amlodipine

To a stirred solution of 100 gm (0.245 moles) of RS amlodipine in 150 ml DMSO was added a solution of 9.2 gm (0.06 moles, 0.25 eq) of L (+) tartaric acid in 100 ml DMSO. The solid starts separating from clear solution within 5–10 mins. This was stirred for 3 hrs and solid was filtered off, washed with acetone and dried to give 58.6 gm (40.5%) R (+) amlodipine hemi L(+) tartarate mono DMSO solvate. mp. 160–162° C., 96.8% d.e. by chiral HPLC.

EXAMPLE 4

S(−)Amlodipine Hemi D(−)Tartarate Mono DMSO Solvate from RS Amlodipine

To a stirred solution of 100 gm (0.245 moles) of RS amlodipine in 500 ml DMSO was added a solution of 9.2 gm (0.06 moles, 0.25 eq) of D(−) tartaric acid in 500 ml DMSO. The solid starts separating from clear solution within 5–10 ml. This was stirred at room temperature overnight and solid was filtered off, washed with =etone and dried to give 47.5 gm (34.6%) S(−) amlodipine hemi D(−) tartarate mono DMSO solvate. mp. 159–161° C., 99.5% d.e. by chiral HPLC.

EXAMPLE 5

S(−)Amlodipine Hemi D(−)Tartarate Mono DMSO Solvate from RS Amlodipine

To a stirred solution of 100 gm (0.245 moles) of RS amlodipine in 250 ml DMSO was added a solution of 9.2 gm (0.06 moles, 0.25 eq) of D(−) tartaric acid in 250 ml DMSO. The solid starts separating from clear solution within 5–10 wins. This was stirred at room temperature overnight and solid was filtered off, washed with acetone and dried to give 56.2 gm (40.8) S (−) amlodipine hemi D(−) tartarate mono DMSO solvate. mp. 159–161° C., 98.4% d.e. by chiral HPLC.

EXAMPLE 6

R(+) Amlodipine Besylate from R(+) Amlodipine Hemi 14+) Tartarate Mono DMSO Solvate 68.8 gm (0.122 mole, 95;2% de) R (+) amlodipine hemi L(+) tartarate mono DMSO solvate prepared as per example 2 was suspended in aqueous isopropanol (70 ml IPA: 250 ml distilled water) and a solution of benzene sulfonic acid (19.35 gm of 90% cal grade, 0.110 mole) in 150 ml water was added. Th reaction mixture was stirred for 2 hrs and the slurry was filtered, washed with distilled water, hexane, the solid was dried under vac. at 40° C. till constant weight to give R(+) amlodipine besylate (63.4 gm, 84.6% yield) 99.3 ec by chiral HPLC.

Microanalysis: C 51.33%, H 6.13%, N 4.62%, S 5.51 Calc. For $C_{20}H_{24}O_5N_2Cl\ C_6H_6O_3S.2.5\ (H_2O)$ C 51.1%, H 5.7%, N 4.58%, S 5.24%.

EXAMPLE 7

R(+) Amlodipine Besylate from R(+) Amlodipine Hemi L(+) Tartarate Mono DMSO Solvate 68.8 gm (0.122 mole, 95.2% de) R (+) amlodipine hemi L(+) tartarate mono DMSO solvate prepared as per example-2 was suspended in aqueous isopropanol (70 ml IPA: 250 ml distilled water) and a solution of benzene sulfonic acid (21.28 gm of 90% technical grade, 0.122 mole)

in 1150 ml water was added. The reaction mixture was stirred for 2 hrs and the slurry was filtered, washed with distilled water, hexane, the solid was dried under vac. at 40° C. till constant weight to give R(+) amlodipine besylate (66.74 gm, 89.1% yield) 98.7 ee by chiral HPLC.

EXAMPLE 8

S(−) Amlodipine Besylate from S(−) Amlodipine Hemi D(−) Tartarate Mono DMSO Solvate 50 gm (0.089 mole) of S (−) amlodipine hemi D(−) tartarate mono DMSO solvate prepared as per example 4 was suspended in aqueous isopropanol (70 ml IPA: 150 ml distilled water) and a solution of benzene sulfuric acid (14.1 gm of 90% technical grade, 0.081 mole) in 100 ml water was added. The reaction mixture was stirred for 2 hrs and the slurry was filtered, washed with distilled water, hexane, the solid was dried under vac. at 40° C. till constant weight to give S (−) amlodipine besylate (47.5 gm 87.2% yield) 99.5 ee by chiral HPLC.

Microanalysis: C 50.91%, H 6.3%, N 4.67%, S 5.91 Calc. For $C_{20}H_{24}O_5N_2Cl\ C_6H_6O_3S.2.5(H_2O)$ C 51.1%, H 5.7%, N 4.58%, S 5.24%.

EXAMPLE 9

S(−) Amlodipine Besylate from S(−) Amlodipine Hemi D(−) Tartarate Mono DMSO Solvate 50 gm (0.089 mole) of S(−) amlodipine hemi D(−) tartarate mono DMSO solvate prepared as per example 4 was suspended in aqueous isopropanol (70 ml IPA: 150 ml distilled water) and a solution of benzene sulfonic acid (15.47 gm of 90% technical grade, 0.089 mole) in 100 ml water was added. The reaction mixture was stirred for 2 hrs and the slurry was filtered, washed with distilled water, hexane the solid was dried under vac at 40° C. till constant weight to give S(−) amlodipine besylate (50.1 gm, 92.1% yield) 99.3 ee by chiral HPLC.

EXAMPLE 10

S(−) Amlodipine Besylate from S(−) Amlodipine Hemi D(.) Tartarate in a DMSO Solvate 50 gm (0.089 mole) of S(−)amlodipine hemi D(−) tartarate mono DMSO solvate prepared as per example 4 was slurried in 200 ml distilled water and solution of benzene sulfonic acid (15.47 gm of 90% a technical grade, 0.089 mole) im 125 ml water was added. The reaction mixture was stirred for 2 hrs and the slurry was filtered, washed with distilled water, hexane, the solid was dried under vac. at 40° C. till constant weight to give S(−) amlodipine besylate (50.1 gm, 92.1% yield) 99.3 ee by chiral HPLC.

EXAMPLE 11

R(+) Amlodipine Besylate from R(+) Amlodipine Hemi L(+) Tartarate Mono DMSO Solvate 68.8 gm (0.122 mole, 95.2% de) R (+) Amlodipine hemi L (+) tartarate mono DMSO solvate prepared as per example 1 was suspended in aqueous isopropanol (90 ml IPA: 250 ml distilled water) and a solution of benzene sulfonic acid (19.35 gm of 90% technical grade, 0.110 mole) in 150 ml water was added. The reaction mixture was stirred for 2 hrs and the slurry was filtered, washed with distilled water, hexane, the solid was dried under vac. at 40° C. till constant weight to give R(+) amlodipine besylate (51.6 gm, 69.4% yield) 99.3 ee by chiral HPLC.

EXAMPLE 12

S(−) Amlodipine Maleate from S(−) Amlodipine Hemi D(−)Tartarate Mon DMSO Solvate S(−) amlodipine hemi D(−)-ta mono DMSO solvate (6.8 gm 0.012 moles) was dissolved in ethanol (10 ml) and maleic acid (1.42 gms 0.012 moles) in 70 ml of water was added with stirring. The separated solid was filtered washed with cold water, washed with hexane and dried under vacuo to give 5.32 gms (82.88%) of S(−) amlodipine maleate, mp. 176–177° C. Optical rotation $[\alpha]'D = -25.10 (c=1, MeOH)$ 98.31 ee.

EXAMPLE 13

S(−) Amlodipine Oxalate from S(−) Amlodipine Hemi D(−)Tartarate Mono DMSO Solvate S(−) amlodipine hemi D(−)-tartarate mono DMSO solvate (6.8 gm, 0.012 moles) was dissolved in ethanol (10 ml) and oxalic acid (1.54 gms 0.012 moles) in 70 ml of water was added with string. The separated solid was filtered washed with cold water, washed with hexane and dried under vacuo to give 5.80 gms (89.2%) of S(−) amlodipine oxalate, mp. 201–203° C. Optical rotation $[\alpha]D = -27.95$ (c=1, MeOH) 98.41 ee.

ADVANTAGES OF THE INVENTION

1. Use of costly resolving agents like camphanic acid, 2-methoxy-2-phenylethanol, cinchonidine is avoided.
2. The use of 0.5 mole of L (+) or D(−) tartaric acid increasing the load of recovery of tartaric acid is avoided.
3. The yield of isolated resolved salt using less quantities of resolving agent is high.
4. The use of large volumes of solvent (1:10) is avoided.
5. The isolation of free chiral base from the salt and treatment with benzene sulfonic acid to get besylate salt is avoided.

We claim:

1. A process for the preparation of pharmaceutically acceptable chiral salts of Amlodipine namely S(−) Amlodipine salts having formula (1) and R(+) Amlodipine salts having formula (2)

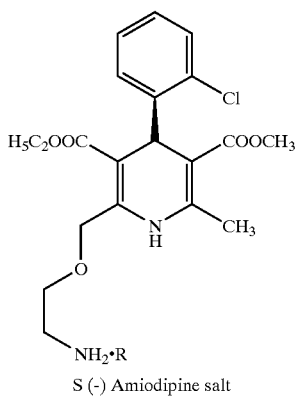

FORMULA-1

S (−) Amlodipine salt

FORMULA-2

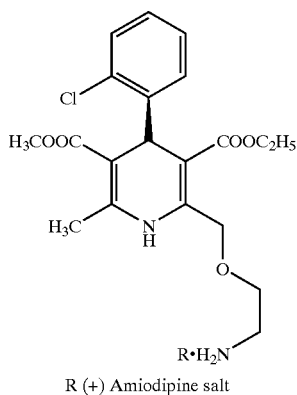

R (+) Amiodipine salt wherein R is selected from the group consisting of benzenesulphoinic acid, succinic acid, malic acid, oxalic acid and p-toluenesulphonicacid, wherein the salts of formula 1 and 2 are prepared without isolation of a free base with optical purity ranging between 96–99% the process comprising:

(a) reacting a solution of RS amlodipine base in an organic solvent with a solution of L(+) or D(−) tartaric acid in an organic solvent at temperature ranging from 20–35° C. for a period ranging between 16–24 hrs., to obtain a solvate comprising an amlodipine tartarate salt;

(b) separating and reacting the amlodipine tartarate salt obtained in step (a) with an aqueous solution of an acid optionally in presence of an organic solvent, and at a temperature ranging between 20–40° C.;

(c) adding water to the reaction mixture of step (b) to obtain the salt of formula 1 and 2, separating the salt of formula 1 and 2 and drying to obtain salt corresponding to the acid used in step (2) with co ranging from 96–99%.

2. A process as claimed in claim 1 wherein the solvent used in step (a) is DMSO.

3. A process as claimed in claim 1 wherein the concentration of RS amlodipine base to solvent (DMSO) ranges between 0.16 to 0.40 gm/ml.

4. A process as claimed in claim 1 wherein the L(+)-tartaric acid or D(−) tartaric acid employed is 0.25 mole equivalent of the amlodipine base.

5. A process as claimed in claim 1 wherein the solvate obtained in step (a) is a precipitate comprising S(−) Amlodipine hemi D(−) tartarate mono DMSO solvate or R(+) amlodipine hemi L(+) tartarate mono DMSO solvate.

6. A process as claimed in claim 1 wherein the solvent used for salt formation in step (b) is selected from dimethylsulfoxide, isopropylacohol and ethanol.

7. A process as claimed in claim 1 wherein the cumulative ratio of water to solvent in steps (b) and (c) ranges between 5:1 to 8:1.

8. A process as claimed in claim 1 wherein the acid used in step (b) is selected from the group consisting of benzenesulfonic, maleic, oxalic acid and p-toluene sulfonic acid.

9. A process as claimed in claim 1 wherein the ratio of amlodipine tartarate salt to organic solvent in step (b) is in the range 1:1 to 1:5.

10. A process as claimed in claim 8 wherein the mole equivalent of benzene sulfonic acid used res between 0.9 to 1.

11. A process as claimed in claim 1 wherein the optical purity of R(+) amlodipine besylate or S(−) amlodipine besylate is improved from 95% to 99%.

* * * * *